United States Patent [19] [11] 3,998,956
Stähle et al. [45] Dec. 21, 1976

[54] PHARMACEUTICAL COMPOSITIONS CONTAINING A 1-(THIENYL-METHYL)-2-ANILINO-2-IMIDAZOLINE AND METHOD OF USE

[75] Inventors: Helmut Stähle; Herbert Köppe; Werner Kummer; Klaus Stockhaus, all of Ingelheim am Rhein, Germany

[73] Assignee: Boehringer Ingelheim GmbH, Ingelheim am Rhein, Germany

[22] Filed: Dec. 10, 1975

[21] Appl. No.: 639,341

Related U.S. Application Data

[62] Division of Ser. No. 441,451, Feb. 11, 1974, Pat. No. 3,939,717.

[30] Foreign Application Priority Data

Feb. 23, 1973 Germany .......................... 2308883

[52] U.S. Cl. ............................................. 424/273
[51] Int. Cl.² ...................................... A61K 31/415
[58] Field of Search ................................... 424/273

Primary Examiner—Stanley J. Friedman
Attorney, Agent, or Firm—Hammond & Littell

[57] ABSTRACT

Pharmaceutical compositions containing as an active ingredient a compound of the formula

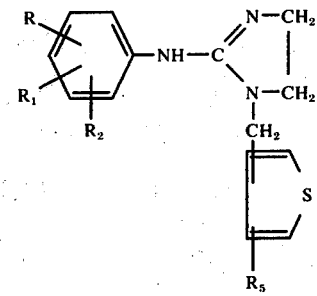

wherein R, $R_1$ and $R_2$ are each hydrogen, fluorine, chlorine, bromine, methyl, ethyl, methoxy, trifluoromethyl or cyano, and $R_5$ is hydrogen, methyl or ethyl, or a non-toxic, pharmaceutically acceptable acid addition salt thereof; and a method of using the same as analgesics and hypotensives.

10 Claims, No Drawings

PHARMACEUTICAL COMPOSITIONS CONTAINING A 1-(THIENYL-METHYL)-2-ANILINO-2-IMIDAZOLINE AND METHOD OF USE

This is a division of copending application Ser. No. 441,451 filed Feb. 11, 1974, now U.S. Pat. No. 3,937,717 granted Feb. 10, 1976.

This invention relates to novel pharmaceutical compositions containing a 1-(thienyl-methyl)-2-anilino-2-imidazoline or a non-toxic acid addition salt thereof, as well as to a method of using the same as analgesics and hypotensives.

More particularly, the present invention relates to phramaceutical dosage unit compositions containing as an active ingredient a compound of the formula

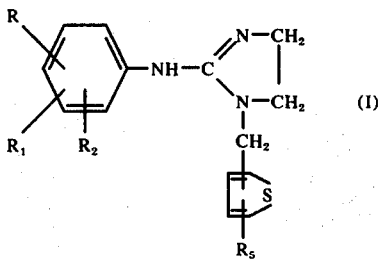

wherein

R, $R_1$ and $R_2$ are each hydrogen, fluorine, chlorine, bromine, methyl, ethyl, methoxy, trifluoromethyl or cyano, and $R_5$ is hydrogen, methyl or ethyl, or a non-toxic, pharmaceutically acceptable acid addition salt thereof.

A subgenus thereunder is constituted by pharmaceutical dosage unit compositions containing as an active ingredient a compound of the formula

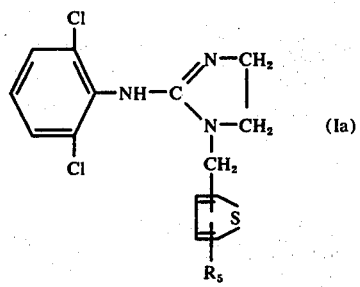

wherein $R_5$ is hydrogen or methyl, or a non-toxic, pharmaceutically acceptable acid addition salt thereof.

Examples of specific compounds of the formula I suitable for use as active ingredients in these compositions are the following:

1-[thienyl-(2)-methyl]-2-(2',6'-dichloro-anilino)-2-imidazoline,
1-[thienyl-(3)-methyl]-2-(2', 6'-dichloro-anilino)-2-imidazoline,
1-[2-methylthienyl-(3)-methyl]-2-(2',6'-dichloro-anilino)-2-imidazoline,
1-[3-methylthienyl-(2)-methyl]-2-(2',6'-dichloro-anilino)-2-imidazoline,
1-[3-methylthienyl-(4)-methyl]-2-(2',6'-dichloro-anilino)-2-imidazoline,
1-[2-methylthienyl-(4)-methyl]-2-(2',6'-dichloro-anilino)-2-imidazoline,
1-[2-methylthienyl-(5)-methyl]-2-(2',6'-dichloro-anilino)-2-imidazoline,
1-[4-methylthienyl-(2)-methyl]-2-(2',6'-dichloro-anilino-2-imidazoline,
1-[2-methylthienyl-(3)-methyl]-2-(2'-chloro-4'-methyl-anilino)-2-imidazoline
1-[2-methylthienyl-(3)-methyl]-2-(2'-chloro-3'-methyl-anilino)-2-imidazoline,
1-[2-methylthienyl-(3)-methyl]-2-(5'-fluoro-2'-methyl-anilino)-2-imidazoline,
1-[2-methylthienyl-(3)-methyl]-2-(2',6'-diethyl-anilino-2-imidazoline,
1-[3-methylthienyl-(2)-methyl]-2-(2',6'-dimethyl-anilino)-2-imidazoline,
1-[3-methylthienyl-(4)-methyl]-2-(2',6'-diethyl-anilino)-2-imidazoline,
1-[3-ethylthienyl-(2)-methyl]-2-(2',6'-dichloro-anilino)-2-imidazoline,
1-[3-ethylthienyl-(2)-methyl]-2-(2',3'-dichloro-anilino)-2-imidazoline,
1-[2-ethylthienyl-(3)-methyl]-2-(2',6'-dichloro-anilino)-2-imidazoline,
1-[2-ethylthienyl-(3)-methyl]-2-(5'-fluoro-2'-methyl-anilino)-2-imidazoline,
1-[2-ethylthienyl-(3)-methyl]-2-(2'-chloro-4-methyl-anilino)-2-imidazoline,
1-[2-ethylthienyl-(3)-methyl]-2-(2'-chloro-3'-methyl-anilino)-2-imidazoline,
1-[3-ethylthienyl-(2)-methyl]-2-(2'-methyl-3'-bromo-anilino)-2-imidazoline, and their non-toxic, pharmaceutically acceptable acid addition salts.

The compounds embraced by formula I may be prepared, inter alia, by reacting a metal salt of a 2-anilino-2-imidazoline of the formula

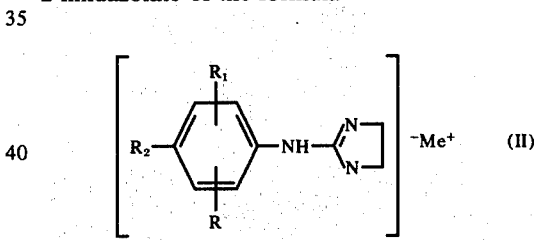

wherein R, $R_1$ and $R_2$ have the meanings previously defined and $Me^{(+)}$ is a metal cation, preferably an alkali metal cation, especially $Na^{(+)}$, with a halide of the formula

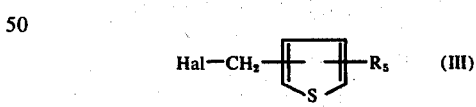

wherein

Hal is chlorine, bromine or iodine, and $R_5$ has the meanings previously defined.

The reaction is carried out most advantageously in a non-polar organic solvent, such as tetrahydrofuran, at elevated temperatures of up to 150° C. The reaction time is usually 1 to 2 hours.

The starting compounds of the formula II may be obtained by reacting a corresponding 2-anilino-2-imidazoline with a metal alkyl or a metal hydride under anhydrous conditions, as illustrated in Example 1 below.

The starting compounds of the formula III may be prepared by known methods, such as halo-methylation of thiophenes or reduction of thiophencarbonate with metal hydrides to hydroxymethyl-thiophenes and subsequent exchange of the hydroxy with halogens. Chloromethylthiophenes may be converted into corresponding bromo- or iodomethyl derivatives by reaction with alkali metal bromides or alkali metal iodides.

2-Anilino-2-imidazolines are described, for example, in Belgian Pat. Nos. 623 305, 687 656, 687 657 and 705 944.

Examples of non-toxic, pharmaceutically acceptable acid addition salts are those formed with a mineral acid, such as hydrochloric acid, hydrobromic acid, hydriodic acid, hydrofluoric acid, sulfuric acid, phosphoric acid or nitric acid, or with an organic acid, such as acetic acid propionic acid, butyric acid, valeric acid, caproic acid, capric acid, oxalic acid, malonic acid, succinic acid, glutaric acid, maleic acid, fumaric acid, lactic acid, tartaric acid, citric acid, malic acid, gluconic acid, benzoic acid, p-hydroxybenzoic acid, phthalic acid, cinnamic acid, salicylic acid, ascorbic acid, 8-chlorotheophylline, methanesulfonic acid or the like.

The following examples illustrate the preparation of compounds of the formula I and non-toxic acid addition salts thereof.

EXAMPLE 1

1-[Thienyl-(3)-methyl]-2-(2',6'-dichloro-anilino)-2-imidazoline hydrobromide 1.3 gm (0.03 mols) of a 55% sodium hydride dispersion were added at 10° to 20° C to a solution of 6.9 gm (0.03 mols) of 2-(2',6'-dichloro-anilino)-2-imidazoline in 50 ml of absolute tetrahydrofuran, and the mixture was stirred for 2 hours at room temperature. A mixture of 5.8 gm (110%) of 3-bromoethyl-thiophene and 10 ml of absolute tetrahydrofuran was added dropwise while stirring, and the resulting mixture was allowed to react at room temperature. The mixture was then refluxed for 3 hours and was then evaporated to dryness under reduced pressure. The residue was admixed with dilute hydrobromic acid, and the resulting precipitate was recovered by vacuum filtration, washed with water and dried. The product was crystallized from absolute methanol to obtain 6.0 gm (49.1% yield) of 1-[thienyl-(3)-methyl]-2-(2',6'-dichloro-anilino)-2-imidazoline hydrobromide melting at 272° to 275° C. Thin layer chromatography showed the compound to be pure, and the product was soluble in dimethylsulfoxide, slightly soluble in ethanol and insoluble in water.

EXAMPLE 2

Using the procedure of Example 1, a 38.6% of yield of 1-[thienyl-(2)-methyl]-2-(2',6'-dichloro-anilino)-2-imidazoline melting at 286°–288° C was obtained.

EXAMPLE 3

Using the procedure of Example 1, a 9.7% yield of 1-[3-methylthienyl-(2)-methyl]-2-(2',6'-dichloro-anilino)-2-imidazoline melting at 273°–276° C was obtained.

The novel analgesic compositions of the invention are comprised of an effective amount of at least one compound of the formula I or a non-toxic, pharmaceutically acceptable acid addition salt thereof and a pharmaceutical carrier. The composition may be in the form of tablets, capsules, suppositories, solutions or powders and may contain other active ingredients. Because of their analgesic and blood pressure reducing properties, the compositions are useful for the treatment of various types of pain, such as migraine headaches, or for the treatment of high blood pressure.

The compositions can be prepared with known galenic excipients, carriers, disintegrating agents, lubricants or sustained release agents.

Tablets may be obtained by mixing the active ingredients with known excipients, for example, with inert diluents, such as calcium carbonate, calcium phosphate or lactose; disintegrants, such as corn starch or alginic acid; binders, such as starch or gelatin; lubricants, such as magnesium stearate or talc; and/or agents for sustained release, such as carboxypolymethylene, carboxymethylcellulose, cellulose acetate phthalate or polyvinylacetate.

The tablets may also have several layers, and coated tablets may be produced by coating cores prepared analogous to the tablets with agents commonly used for coating tablets, such as polyvinylpyrrolidone, shellac, gum arabic, talcum, titanium dioxide or sugar. To obtain sustained release or to avoid incompatibilities, the core may also consist of several layers. The tablet-core is preferably made of several layers to obtain sustained release whereby the auxiliaries mentioned above for the tablets may be used.

For production of soft gelatin capsules or of similar sealed capsules, the active substance may be admixed with a plant oil. Hard gelatin capsules may contain granulates of the active substance with solid carriers in powder form such as lactose, saccharose, sorbitol, mannitol, starch such as potato starch, corn starch or amylopetin, cellulose derivatives or gelatin.

Syrups of the active ingredients of the invention or active ingredient combinations may also contain a sweetner such as saccharin, cyclamate, glycerin or sugar, as well as an agent improving the taste such as flavors like vanillin or orange extract. They may also contain suspension auxiliaries or thickeners, such as sodium carboxymethylcellulose, wetting agents such as condensation products of fatty alcohols with ethylene oxide, or preservatives such as alkyl p-hydroxy-benzoates.

Injectable solutions or suspensions may be produced in the conventional way such as with the use of preservatives such as alkyl p-hydroxybenzoates, or stabilizers such as complexons and they are then added under sterile condition into injection vials or ampules. The solution may also contain stabilizers and/or buffers.

The suppositories may be produced, for example, by mixing the active ingredient or active ingredient combinations with conventional carriers such as neutral fats or polyethyleneglycol or derivatives thereof. Gelatin capsules for rectal administration containing the active substance in admixture with plant oil or paraffin oil may be produced as well.

The novel method of the invention for relieving pain and/or reducing blood pressure in warm-blooded animals comprises administering to warm-blooded animals an effective amount of at least one compound of the formula I or a non-toxic, pharmaceutically acceptable acid addition salt thereof. The compounds may be administered parenterally or enterally. The usual daily dose is 1 to 30 mgm/kg depending upon the method of administration and the specific compound.

The following examples illustrated a few pharmaceutical dosage unit compositions comprising a compound of the formula I or a non-toxic, pharmaceutically acceptable acid addition salt thereof as an active ingredient and represent the best modes contemplated of putting the invention into practical use. The parts are parts by weight unless otherwise specified.

EXAMPLE 4

Tablets weighing 445 mg were prepared by intimately admixing 30 mg of 1-(thienyl-(2)-methyl)-2-(2',6'-dichloro-anilino)-2-imidazoline, 160 mgm of corn starch, 250 mgm of secondary calcium phosphate and 5 mgm of magnesium stearate, and the mixture was granulated and pressed into tablets containing 30 mgm of the active compound.

EXAMPLE 5

Gelatin capsules weighing 200 mgm were prepared by well mixing of 25 mg of 1-(thienyl-(3)-methyl)-2-(2,6-dichlorophenylamino)-2-imidazoline hydrobromide and 175 mgm of corn starch and filling the capsules.

EXAMPLE 6

1.5 parts by weight of 1-[thienyl-(2)-methyl]-2-(2',-6'-dichloro-anilino)-2-imidazoline and 0.2 parts by weight of the sodium salt of the ethylenediaminetetraacetic acid were dissolved in sufficient water, and water was added to obtain a final volume of 100.0 parts by weight. The solution was filtered free of suspended particles and filled into 2 ccm-ampules under aseptic conditions. Then the ampules were sterilized and sealed, and each ampule contained 20 ml of the active ingredient.

Analogous compositions are obtained when any one of the other 2-anilino-2-imidazolines embraced by formula I or a non-toxic, pharmaceutically acceptable acid addition salt thereof was substituted for the particular active ingredient in Examples 4 through 6. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. An analgesic or hypotensive pharmaceutical dosage unit composition consisting essentially of an inert pharmaceutical carrier and an effective analgesic or hypotensive amount of a compound of the formula

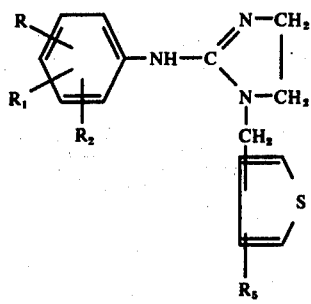

wherein
R, $R_1$ and $R_2$ are each hydrogen, fluorine, chlorine, bromine, methyl, ethyl, methoxy, trifluoromethyl or cyano, and
$R_5$ is hydrogen, methyl or ethyl, or a non-toxic, pharmaceutically acceptable acid addition salt thereof.
2. A composition of claim 1, wherein said compound is one of the formula

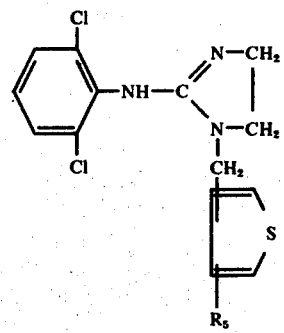

wherein $R_5$ is hydrogen or methyl, or a non-toxic, pharmaceutically acceptable acid addition salt thereof.
3. A composition of claim 1, wherein said compound is 1-[thienyl-(3)-methyl]-2-(2',6'-dichloro-anilino)-2-imidazoline or a non-toxic, pharmaceutically acceptable acid addition salt thereof.
4. A composition of claim 1, wherein said compound is 1-[thienyl-(2)-methyl]-2-(2',6'-dichloro-anilino)-2-imidazoline or a non-toxic, pharmaceutically acceptable acid addition salt thereof.
5. A composition of claim 1, wherein said compound is 1-[3-methylthienyl-(2)-methyl]-2-(2',6'-dichloro-anilino)-2-imidazoline or a non-toxic, pharmaceutically acceptable acid addition salt thereof.
6. The method of relieving pain or lowering the blood pressure in a warm-blooded animal in need of such treatment, which comprises parenterally or enterally administering to said animal a compound of the formula

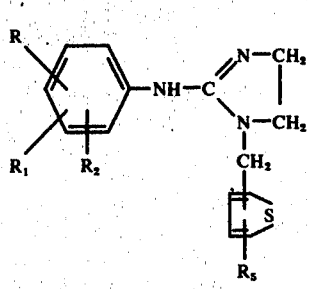

wherein
R, $R_1$ and $R_2$ are each hydrogen, fluorine, chlorine, bromine, methyl, ethyl, methoxy, trifluoromethyl or cyano, and
$R_5$ is hydrogen, methyl or ethyl, or a non-toxic, pharmaceutically acceptable acid addition salt thereof.
7. The method of claim 6, wherein said compound is of the formula

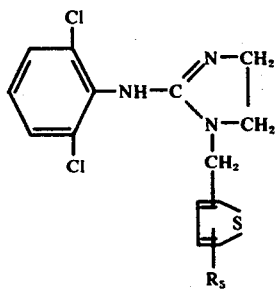

wherein R$_5$ is hydrogen or methyl, or a non-toxic, pharmaceutically acceptable acid addition salt thereof.

8. The method of claim 6, wherein said compound is 1-[thienyl-(3)-methyl]-2-(2',6'-dichloro-anilino)-2-imidazoline or a non-toxic, pharmaceutically acceptable acid addition salt thereof.

9. The method of claim 6, wherein said compound is 1-[thienyl-(2)-methyl]-2-(2',6'-dichloro-anilino)-2-imidazoline or a non-toxic, pharmaceutically acceptable acid addition salt thereof.

10. The method of claim 6, wherein said compound is 1-[3-methylthienyl-(2)-methyl]-2-(2',6'-dichloro-anilino)-2-imidazoline or a non-toxic, pharmaceutically acceptable acid addition salt thereof.

* * * * *